United States Patent
Stearns et al.

(10) Patent No.: US 6,307,203 B1
(45) Date of Patent: Oct. 23, 2001

(54) DATA BINNING METHOD AND APPARATUS FOR PET TOMOGRAPHY

(75) Inventors: Charles W. Stearns, New Berlin; William J. Bridge, Watertown, both of WI (US)

(73) Assignee: GE Medical Systems Global Technology Company LLC, Waukesha, WI (US)

(*) Notice: Subject to any disclaimer, the term of this patent is extended or adjusted under 35 U.S.C. 154(b) by 0 days.

(21) Appl. No.: 09/200,289

(22) Filed: Nov. 25, 1998

(51) Int. Cl.[7] ................................................ G01T 1/166

(52) U.S. Cl. ........................ 250/363.03; 250/363.04; 250/363.09

(58) Field of Search ..................... 250/363.03, 363.09, 250/363.04; 600/447, 448, 449; 712/11

(56) References Cited

U.S. PATENT DOCUMENTS 5,272,343    12/1993    Stearns .................... 250/363.03

Primary Examiner—Georgia Epps
Assistant Examiner—Richard Hanig
(74) Attorney, Agent, or Firm—Michael A. Jaskolski; Christian G. Cabou

(57) ABSTRACT

A method for reducing required memory in a PET acquisition system processor wherein imaging data is collected and binned in a two dimensional histogram of coincident counts, the two dimensions being a flight path angle $\theta$ and a distance R from the center of an imaging area, the method including the steps of determining when data acquired at a current acquisition angle will not include data corresponding to a specific flight angle and, when this is the case, storing the data corresponding to the specific flight angle on a secondary memory storage device independent of the processor memory. The method also includes a back projection method for using the stored data to construct an image and the invention includes an apparatus for performing the method.

17 Claims, 5 Drawing Sheets

DATA BINNING METHOD AND APPARATUS FOR PET TOMOGRAPHY

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to positron emission tomography (PET) and more specifically to a method for storing collected imaging data to a stand alone memory device during data acquisition so as to reduce the amount of memory required by a processor to acquire an entire set of imaging data.

Positrons are positively charged electrons which are emitted by radionuclides which have been prepared using a cyclotron or other device. The radionuclides most often employed in diagnostic imaging are fluorine-18 ($^{18}$F), carbon-11 ($^{11}$C), nitrogen-13 ($^{13}$N), and oxygen-15 ($^{15}$O). Radionuclides are employed as radioactive tracers called "radiopharmaceuticals" by incorporating them into substances such as glucose or carbon dioxide. One common use for radiopharmaceuticals is in the medical imaging field.

To use a radiopharmaceutical in imaging, the radiopharmaceutical is injected into a patient and accumulates in an organ, vessel or the like, which is to be imaged. It is known that specific radiopharmaceuticals become concentrated within certain organs or, in the case of a vessel, that specific radiopharmeceuticals will not be absorbed by a vessel wall. The process of concentrating often involves processes such as glucose metabolism, fatty acid metabolism and protein synthesis. Hereinafter, in the interest of simplifying this explanation, an organ to be imaged will be referred to generally as an "organ of interest" and prior art and the invention will be described with respect to a hypothetical organ of interest.

After the radiopharmaceutical becomes concentrated within an organ of interest and while the radionuclides decay, the radionuclides emit positrons. The positrons travel a very short distance before they encounter an electron and, when the positron encounters an electron, the positron is annihilated and converted into two photons, or gamma rays. This annihilation event is characterized by two features which are pertinent to medical imaging and particularly to medical imaging using photon emission tomography (PET). First, each gamma ray has an energy of essentially 511 keV upon annihilation. Second, the two gamma rays are directed in substantially opposite directions.

In PET imaging, if the general locations of annihilations can be identified in three dimensions, the shape of an organ of interest can be reconstructed for observation. To detect annihilation locations, a PET camera is employed. An exemplary PET camera includes a plurality of detectors and a processor which, among other things, includes coincidence detection circuitry. Each time a 511 keV photon impacts a detector, the detector generates an electronic signal or pulse which is provided to the processor coincidence circuitry.

The coincidence circuitry identifies essentially simultaneous pulse pairs which correspond to detectors which are generally on opposite sides of the imaging area. Thus, a simultaneous pulse pair indicates that an annihilation has occurred on a straight line between an associated pair of detectors. Over an acquisition period of a few minutes millions of annihilations are recorded, each annihilation associated with a unique detector pair. After an acquisition period, recorded annihilation data is used via any of several different well known procedures to construct a three dimensional image of the organ of interest.

PET cameras have been configured in many geometries. Because annihilation data has to be collected from essentially 360 degrees about an organ which is to be imaged, one popular PET camera configuration includes small detectors arranged to form an annular gantry about the imaging arc. In this case data from all required degrees can be collected at the same time, separated into data from different angles about the imaging area and then back projected as different profile type views to form the tomographic image. Unfortunately annular cameras require large numbers of detectors and therefore are extremely expensive which renders annular cameras unsuitable for many applications.

Referring to FIG. 1, another common PET camera configuration 10 includes first and second cameras 12, 14, respectively, each camera 12, 14 including a flat impact surface 13, 15, respectively, for detecting impacting gamma rays. Each camera 12 and 14 is characterized by a width W across which hardware which can distinguish M different impact locations is arranged. To detect coincident gamma ray pairs, first and second cameras 12 and 14 are positioned a distance D apart and such that surfaces 13 and 15 oppose each other on opposite sides of an imaging area 16 and define a field of view (FOV). With the opposing camera configuration, instead of collecting tomographic data from all angels about imaging area 16 simultaneously as with an annular configuration, during an acquisition session, first and second cameras 12 and 14 are rotated (see arrows 18, 20) about imaging area 16 through approximately 180 degrees, the cameras maintained at different stop angles for short acquisition periods which together comprise the acquisition session.

For the purposes of this explanation the term "profile view" or simply "view" will be used to describe all annihilation data collected during a data acquisition period which emanates from the imaging area along parallel paths. At each camera position, cameras 12 and 14 collect annihilation data corresponding to several different profile views. A more detailed analysis of FIG. 1 can be used to better understand profile views and how data corresponding to several views is collected at each camera position.

Referring to FIG. 1, an initial camera position angle $\theta$o is defined by a line between and perpendicular to impact surfaces 13 and 15. During rotation, a stop angle $\theta$s is defined by the angle between the initial position angle $\theta$o and the instantaneous line between and perpendicular to impact surfaces 13 and 15. While some systems operate with a continuously changing stop angle $\theta$s during data acquisition, unless indicated otherwise and in the interest of simplifying this explanation, it will be assumed that an exemplary system actually stops at different stop angles and only acquires data while stationary.

Referring still to FIG. 1, assuming cameras 12 and 14 are in the initial position illustrated so that stop angle $\theta$s is zero degrees, if an annihilation event occurs at the center of imaging area 16 as indicated by point 22, the annihilation event may generate a corresponding gamma ray pair which emanates along virtually any path. However, with cameras 12 and 14 positioned as illustrated, cameras 12 and 14 can only collect generated gamma rays if the rays are directed within an angle range between a maximum negative flight path angle $-\theta m$ and a maximum positive flight path angle $+\theta m$ (and within a z-axis plane which is perpendicular to the illustration). In the interest of simplifying this explanation it will be assumed that cameras 12 and 14 are single dimensional (i.e. z=1) and, although range $-\theta m$ through $+\theta m$ may span several different ranges, it will be assumed that range $-\theta m$ through $+\theta m$ spans 30° (i.e. 15° on either side of an instantaneous stop angle $\theta s$).

Referring also to FIG. 2, assume the annihilation event at point 22 (i.e. a center of imaging area 16) which is being studied generates gamma rays which are directed along the a flight path 50 which is parallel to initial position angle $\theta o$. In addition, assume that other annihilation events occur at other positions indicated at points 24, 26, 28, 30 and 32 and that each of those events, like the event at point 22, generates a pair of gamma rays which emanate along flight paths parallel to path 50. Because all of the ray pairs in FIG. 2 are parallel, the pairs together form a profile view of data, in essence indicating what the collected data "appears" like from a view which is perpendicular to the gamma ray flight paths. For the purposes of this explanation the profile view corresponding to the flight path illustrated in FIG. 2 will be referred to as a first profile view.

While some gamma rays are traveling along the paths indicated in FIG. 2 during a data acquisition period, other gamma rays travel along other flight paths. For example, referring also to FIG. 3, annihilation events are indicated at points 34, 36, 38 and 40, each of which causes gamma rays having flight paths which cause rays to impact surfaces 13 and 15 at a projection ray angle $\theta f$. Because all of the ray pairs in FIG. 3 are parallel, the pairs together form a profile view of data, in essence indicating what the collected data "appears" like from a view which is perpendicular to the gamma ray flight paths. For the purposes of this explanation the profile view corresponding to the flight path illustrated in FIG. 3 will be referred to as a second profile view.

Thus, annihilation data corresponding to two different profile views is collected simultaneously while cameras 12 and 14 are at the initial position illustrated in FIGS. 2 and 3. In fact, for every angle within range $-\theta m$ to $+\theta m$, data is collected for a separate profile view corresponding to the angle, the number of angles limited only by the ability of camera 12 and 14 hardware to distinguish between angles. For example, when collecting data at the initial position illustrated, data corresponding to one thousand different profile views might be collected.

To distinguish between data from different profile views, collected annihilation data is stored as a function of two coordinates, a first coordinate, a projection ray angle $\theta f$, indicating the projection ray path associated with a specific profile view and a second coordinate, a distance R, indicating the location of the projection ray path within the profile view. For example, referring still to FIG. 3, the annihilation event which occurs at point 38 is associated with projection ray angle $\theta f1$ which is a distance R1 from imaging area central point 22. Other events illustrated in FIG. 3 are characterized by the same projection ray angle $\theta f1$ but different distances R. Similarly, referring to FIG. 2, the annihilation event which occurs at point 30 is characterized by a projection ray angle coordinate $\theta f2$ (not illustrated) which is zero and a distance R2.

During data acquisition coincident counts are organized in a processor memory as a set of two-dimensional arrays, one array for each profile view, each array having as one of its dimensions projection ray angle $\theta f$ and the other dimension distance R.

While annihilation data is collected which corresponds to many different profile views at each stop angle, there is no stop angle at which all data corresponding to a single profile view is collected. For example, referring again to FIG. 2, when cameras 12 and 14 are positioned at the initial stop angle (i.e. $\theta s=0$), the event at point 30 is detected and data associated therewith is stored in a corresponding coincident count associated with angle $\theta f2$ and distance R2. When cameras 12 and 14 are rotated to a different stop angle indicated in phantom and by numerals 12' and 14', an annihilation event at point 30 which generates gamma rays having the projection ray path illustrated still impacts both cameras 12' and 14' causing an annihilation detection which corresponds to the first profile view discussed above. This annihilation detection or event is added to the coincident count corresponding to angle $\theta f2$ and distance R2 as illustrated in FIG. 2.

Referring again to FIG. 1, after data is collected at the initial camera position illustrated, cameras 12 and 14 are rotated through a small angle in a clockwise direction to a second stop angle. For the purposes of this explanation it will be assumed that the stop angle increment in between consecutive stop angles is 2 degrees. Thus, while the initial stop angle corresponds to a zero degree position, the second stop angle corresponds to a 2° position, the third stop angle corresponds to a 4 degree position and so on.

It should be apparent that, after cameras 12 and 14 are rotated to the second stop angle, range $-\theta m$ to $\theta m$ changes such that, upon commencing data acquisition at the new stop angle, no data is collected at original angle $-\theta m$. Similarly, each time the stop angle is changed by clockwise rotation to a new stop angle, angle $-\theta m$ changes and data is not collected at the previous angle $-\theta m$ during the next acquisition period. For example, where the range $-\theta m$ through $\theta m$ is 30°, the range $-\theta m$ through $\theta m$ is $-15°$ through 15° during data acquisition at the initial stop angle. At the second stop angle where $\theta s=2°$, range $-\theta m$ through $\theta m$ is between $-13$ and 17° and so on. During acquisition at the second stop angle data is not collected which corresponds to initial angle $-\theta m$ (i.e. $-15°$) while data is collected which corresponds to angle $-\theta m=-13°$. Hence, more data is collected which corresponds to angle $-13°$ than corresponds to angle $-15°$.

It should be appreciated that only incomplete data corresponding to projection ray angles between $-15$ and $+15°$ is acquired during the first half of an acquisition session. The dearth of data for initial projection ray angles $\theta f$ between $-15°$ and $+15°$, if not supplemented, reduces resulting image quality. To complete data between projection ray angles $-15°$ and $+15°$, additional data is collected at the end of a data acquisition session when the stop angle exceeds $180-2\theta m$ degrees. In the present case, where range $-\theta m$ through $\theta m$ is 30°, data collection to complete projection ray coincident counts for projection rays having angles between $-15°$ and 15° begins when the stop angle is 150°. When the stop angle exceeds 150°, annihilation events along original angle $-\theta m$ (i.e. $-15°$) are again detected and corresponding coincident counts associated with projection ray angle $-\theta m$ are increased. This process of supplementing the $-15°$ to 15° projection ray coincident counts continues through a stop angle equal to $180-\theta in$ degrees. In the present case, because stop angle increment $\theta in$ is 2°, data acquisition continues through 178°.

Thus, data corresponding to initial angle $-\theta m$ and distance R is not completed until after essentially 180° of data acquisition. In conventional data acquisition systems the processor which collects coincident count data effectively maintains coincident count data for each possible projection ray (R, θf) during data acquisition and modifies counts for each ray (R, θf)) as data is collected.

Over the course of 180° of data acquisition, in histogram space, the effect of the acquisition protocol described above is schematically illustrated in FIG. 4 which shows an exemplary histogram 70 having flight angle θf and stop angle θs along the vertical axis and distance R along the horizontal axis. During a data acquisition, cameras 12 and 14 rotate through stop angles ranging from 0 to 178°. At each stop angle θs, a diamond shaped region of coincident count data is acquired, each point within a diamond shaped region representing a separate coincident count coordinate (R, θf). For example, in FIG. 4 the diamond shaped region corresponding to data acquisition at the initial stop angle θs (as illustrated in FIG. 1) where θs is 0° is identified by numeral 44. As indicated above, at the initial stop angle θs coincident count data is collected which corresponds to gamma ray flight paths having projection ray angles between –θm and θm degrees.

For projection ray angles θf equal to angles –θm or θm, while cameras 12 and 14 are at the initial stop angle the only possible value for distance R is zero. Thus, as illustrated in FIG. 4, at angle –θm which is at the top of diamond shaped region 44, region 44 is restricted indicating that data corresponding to a single coincident count is stored for angle –θm at the first stop angle. Similarly, at angle θm which is at the bottom of diamond shaped region 44, region 44 is restricted indicating that data corresponding to a single coincident count is stored for angle θm at the initial stop angle.

Referring to FIGS. 1 and 2, while the cameras are at the initial stop angle θs=0°, for projection rays having angles θf equal to 0° so that associated rays are perpendicular to impact surfaces 13 and 15, data is collected for all distance R values between –W/2 and W/2. Thus, referring also to FIG. 4, at the initial stop angle θs, data corresponding to coincident counts associated with projection rays having angles θf equal to 0° are represented by a horizontal line which bisects region 44 and extends between distance R=–W/2 and distance R=W/2.

For every projection ray angle θf between initial angle –θm and 0° there are a number of distances R, the number of distances R depending on how close a specific flight angle θf is to 0°. The number of R coordinates for a specific projection ray angle θf increases as the projection ray angle θf gets closer to 0°. Similar comments can be made with respect to the histogram space between 0° and θm. Thus, region 44 is diamond shaped because there are a large number of R values at 0° angles θf, a single R value at each of angles θf equal to –θm and θm and a linearly decreasing number of R values between the 0° angle θf and angles –θm and θm.

Referring still to FIG. 4, at the second stop angle (i.e. a 2 degree stop angle in the present example), a second diamond shaped region 44' of data is acquired. The shape of region 44' is identical to the shape of region 44, the only difference being that region 44' is shifted 2° along the vertical axis. At the second stop angle, while many of the projection ray angles for which data is collected are the same as during acquisition at the first stop angle, some of the projection ray angles are different. Specifically, the range of projection ray angle acquisition is (–θm+2°) through (θm+2°).

As stop angles are changed to acquire data from different perspectives about imaging area 16, the diamond shaped region is shifted down the vertical axis until the stop angle is equal to 178°. Because range –θm through θm is 30°, the range during data acquisition at the final stop angle is between 163° and 193° and the entire data set illustrated in FIG. 4 extends from –15° to 193° (i.e. approximately –θm through 180+θm degrees).

One problem with PET imaging systems is that the amount of data which must be acquired during data acquisition is extremely large and therefore a huge memory is required. One solution for reducing memory size is to generate data in a compact histogram form. To this end, referring again to FIG. 4, the symmetrical relationship P(R, θf)=P(–R, θf180) between polar coordinate data can be used to store coincident counts corresponding to projection ray angles θf which are less than 0° or greater than 180°, to projection ray coincident counts which are within the 0° to 180° range. This compacting is represented by arrows 60 and 62 and results in the compact histogram form 72 illustrated in FIG. 4. For example, referring again to FIG. 1, rays along projection ray paths having projection ray angles θf of –15° (i.e. the initial –θm angle) are outside the compact histogram form 72. This data can be directed to a histogram address within compact histogram form 72 by changing the sign of distance R and adding 180° to angle –θm. The new angle is 165° which is within compact form 72.

Unfortunately the compact histogram solution has several shortcomings. First, while the mathematics to convert data which is outside the compact form into data which is inside the compact form is relatively simple to derive, solving the mathematics in real time to form the compact histogram during the acquisition process is impractical for a number of reasons. As an initial matter, the arithmetic required for the conversion is relatively involved due at least in part to the fact that data from outside the compact form must be reflected about the distance R=0 axis which requires a plurality of conditional steps. In addition, although possible, it would be extremely difficult to provide a lookup table for conversion of all coincident detection pair possibilities and stop angles to distance R and projection ray angle θf possibilities. Moreover, as some systems change stop angle θs continuously during data acquisition, even if it where possible to provide a suitable lookup table, it may be impossible to update using a lookup table whenever stop angle θs changes.

A second and perhaps more vexing problem with forming a compact histogram form is that such a form makes it extremely difficult to save any collected data to an inexpensive stand alone storage device which could alleviate some of the burden on the processor's memory. Storage outside a processor memory during acquisition is difficult because coincident counts for some coordinates (R, θf) must be maintained during an entire acquisition session. For example, as described above, data acquired at the initial stop angle θs is not completed until acquisition at the final stop angle is completed at the end of an acquisition session. Because coincident counts for some coordinates have to be maintained throughout an acquisition session, it is extremely difficult to define an acquisition regime which saves raw data to a stand alone storage device during acquisition.

BRIEF SUMMARY OF THE INVENTION

It has been recognized that during a data acquisition session much of the data which has conventionally been maintained in a processor's memory is not updated during identifiable intervals of the acquisition process. It has also been recognized that coincident count data for a specific projection ray (R, θf) can be stored as two different coincident counts and the counts can be combined during image construction back projection without affecting image quality. These realizations lead to two conclusions. First, coincident counts which are not to be updated for an extended period can be stored to a secondary storage device and do not have to be maintained in a processors' memory. Second, even where a specific coincident count is to be modified during a subsequent but distant time interval, the specific coincident count can be stored to the secondary storage device thereby further freeing processor memory. By programming a data sorter to take advantage of the conclusions above, the size of the processor memory which is required to acquire PET data can be substantially reduced or, in the alternative, the memory can be used to facilitate other processor functions.

In addition, because much of the specific coincident count data is stored to a secondary storage device during data acquisition thereby freeing up processor memory, the processor need not form a compact histogram to accommodate all data during acquisition. In fact, the histogram which is formed in the secondary storage device is not compact. Nevertheless, because secondary storage device space is relatively plentiful and can be supplemented relatively inexpensively, an expanded histogram stored on the secondary device is not an extreme burden.

Specifically, the invention includes a method to be used with a PET system, the system including two PET cameras, a processor including processor memory and a secondary memory. Each camera has a flat impact surface and is positioned such that the impact surfaces are parallel to each other on opposite sides of an imaging area through which a rotation axis passes. The cameras are mounted for rotation among a plurality of stop angles about the axis for acquiring PET imaging data throughout an arc about the axis. At each stop angle, the cameras collecting data corresponding to an acquisition angle range including flight path angles between a maximum positive flight path angle and a maximum negative flight path angle which correspond to the stop angle. The method is for reducing the amount of processor memory required to acquire PET imaging data. An instantaneous stop angle and an instantaneous acquisition angle range are a current stop angle and a current range, respectively. An acquisition range immediately preceding the current range is a previous range. The method comprises the steps of prior to gathering imaging information at a current stop angle, for each flight path angle within the previous range, determining if additional data will be collected during data acquisition at the current stop angle and at the next consecutive Q stop angles; where imaging data for an acquisition angle will be collected during data acquisition at the current or next consecutive Q stop angles, maintaining imaging data for the acquisition angle in the processor memory; and where imaging data for an acquisition angle will not be collected during data acquisition at the current or next consecutive Q stop angles, storing the imaging data for the acquisition angle in the secondary memory.

In one embodiment Q is equal to the number of remaining stop angles at which imaging data is to be gathered. However, in a preferred embodiment Q is 1.

In one aspect, each impact surface is characterized by a width which extend between first and second opposite surface edges, the cameras mounted such that the first edges and second edges of each camera oppose each other, respectively. The cameras are mounted for 180° of rotation about the imaging axis. When the cameras are in an initial position an initial system axis passes through the imaging axis and is perpendicular to each of the impact surfaces bisecting each impact surface and forming an initial system angle. A stop angle is defined by the initial angle plus some offset angle, an extreme negative flight path angle is defined by the angle formed by the stop angle and a plane which extends between the first edge of the first camera impact surface and the second edge of the second camera impact surface and an extreme positive flight path angle is defined by the angle formed by the stop angle and a plane which extends between the second edge of the first camera impact surface and the first edge of the second camera impact surface. The acquisition angle range is among the angles between the extreme maximum and minimum flight path angles.

In one embodiment the acquisition angle range is defined by the extreme maximum and minimum flight path angles.

The inventive method may also be for, after the imaging data has been stored in the secondary memory, constructing an image using the stored imaging data, the method further including the steps of, filtering the imaging data and back-projecting the data to construct the image.

DETAILED DESCRIPTION OF THE INVENTION

I. HARDWARE

Figure 6:
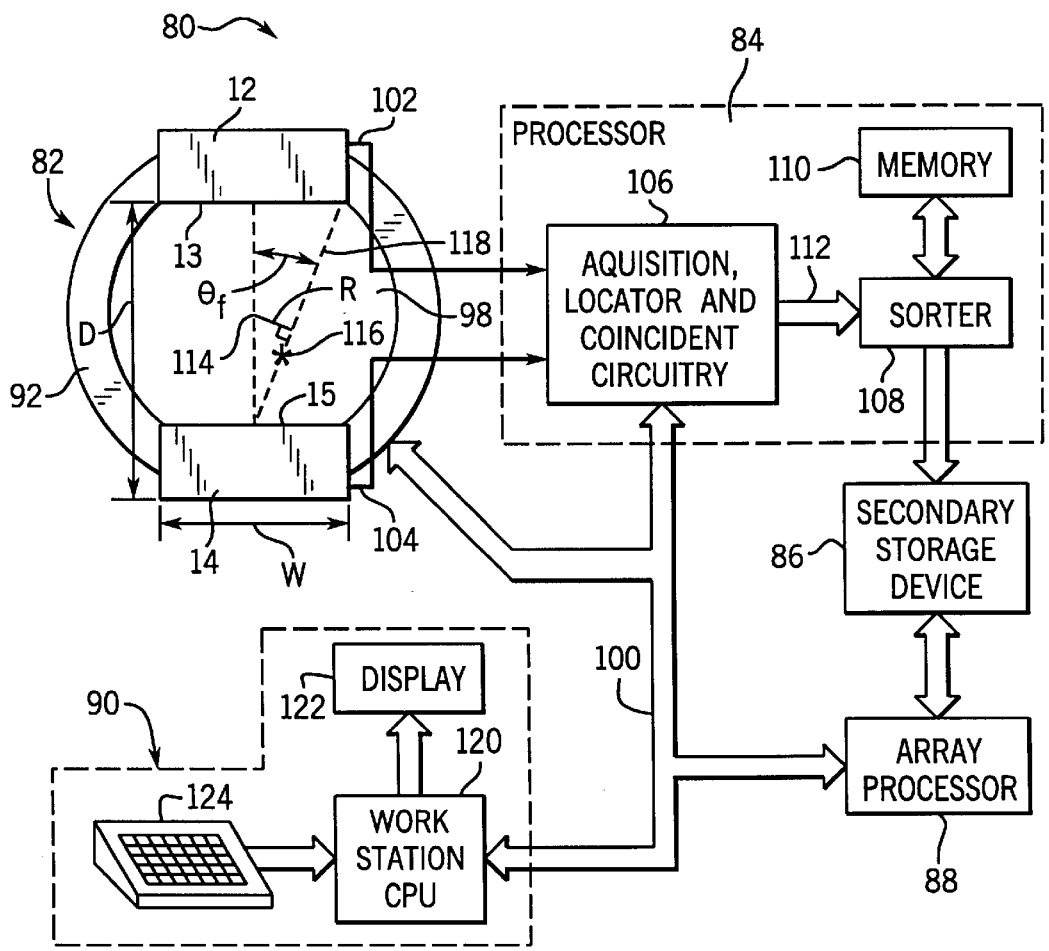
FIG. 6 is a schematic diagram illustrating the components of the inventive PET system.

Referring now to the drawings, wherein like reference characters and symbols represent corresponding elements and signals throughout the several views, and more specifically referring to FIG. 6, the present invention will be described in the context of an exemplary PET scanner system 80. System 80 includes an acquisition system 82, an operator work station 90, a data acquisition processor 84, a secondary storage device 86 and an array processor 88.

System 82 includes a gantry 92 which supports first and second gamma cameras 12 and 14 about a central bore which defines an imaging area 98. Each camera 12,14 has a width W and cameras 12 and 14 are separated by a distance D. A patient table (not illustrated) is positioned in front of gantry 92 and is aligned with imaging area 98. A patient table controller (also not illustrated) moves a table bed into imaging area 98 in response to commands received from work station 90.

A gantry controller (not illustrated) is mounted within gantry 92 and is responsive to commands received from operator work station 90 through a serial communication link 100 to operate gantry 92. For example, gantry 92 can be tilted away from vertical on command from an operator, can perform a "transmission scan" with a calibrated radio nuclide source to acquire attenuation measurements, can perform a "coincidence timing calibration scan" to acquire corrective data, or can perform a normal "emission scan" in which positron annihilation events are counted.

Construction and operation of an exemplary PET camera 12 and 14 is described in detail in U.S. Pat. No. 5,272,343 which issued on Dec. 21, 1993 and is entitled "Sorter for Coincidence Timing Calibration in PET Scanner" and which is incorporated herein by reference. Each of cameras 12 and 14 generates analog signals when a gamma ray is detected. The analog signals are provided to processor 84 via data buses 102 and 104.

Processor 84 includes acquisition, event locator and coincident (ALC) circuitry 106, a sorter 108 and a processor memory 1 10. ALC circuitry 106 receive the analog signals via buses 102 and 104 and perform several different functions. First, ALC circuitry 106 identifies the total energy associated with a perceived event and compares the total energy to an expected range of energies corresponding to a likely true annihilation event. To this end, the expected energy range of a true annihilation event is typically 511 keV±20%. ALC circuitry 106 discards perceived events which are outside the expected range.

Second, ALC circuitry 106 determines the location on a camera impact surface 13, 15 at which a gamma ray was detected and the exact time at which a gamma ray was detected. Methods to determine impact location are well known in the PET imaging art.

Third, ALC circuitry 106 determines if any two events (i.e. detected gamma rays) are in coincidence. Coincidence is determined by a number of factors. First, the time markers in each event data packet must be within a specified time interval (e.g. 12.5 nanoseconds) of each other, and second, the locations indicated by the two event data packets must lie on a straight line which passes through the field of view (FOV) in imaging area 98. Events which cannot be paired as coincidence events are discarded, but coincidence event pairs are located and recorded as a coincidence data packet that is conveyed through a serial link 112 to sorter 108. Each coincidence data packet includes a pair of digital numbers which precisely identify the locations of coincident events on each of first and second cameras 12, 14, respectively.

Figure 7:
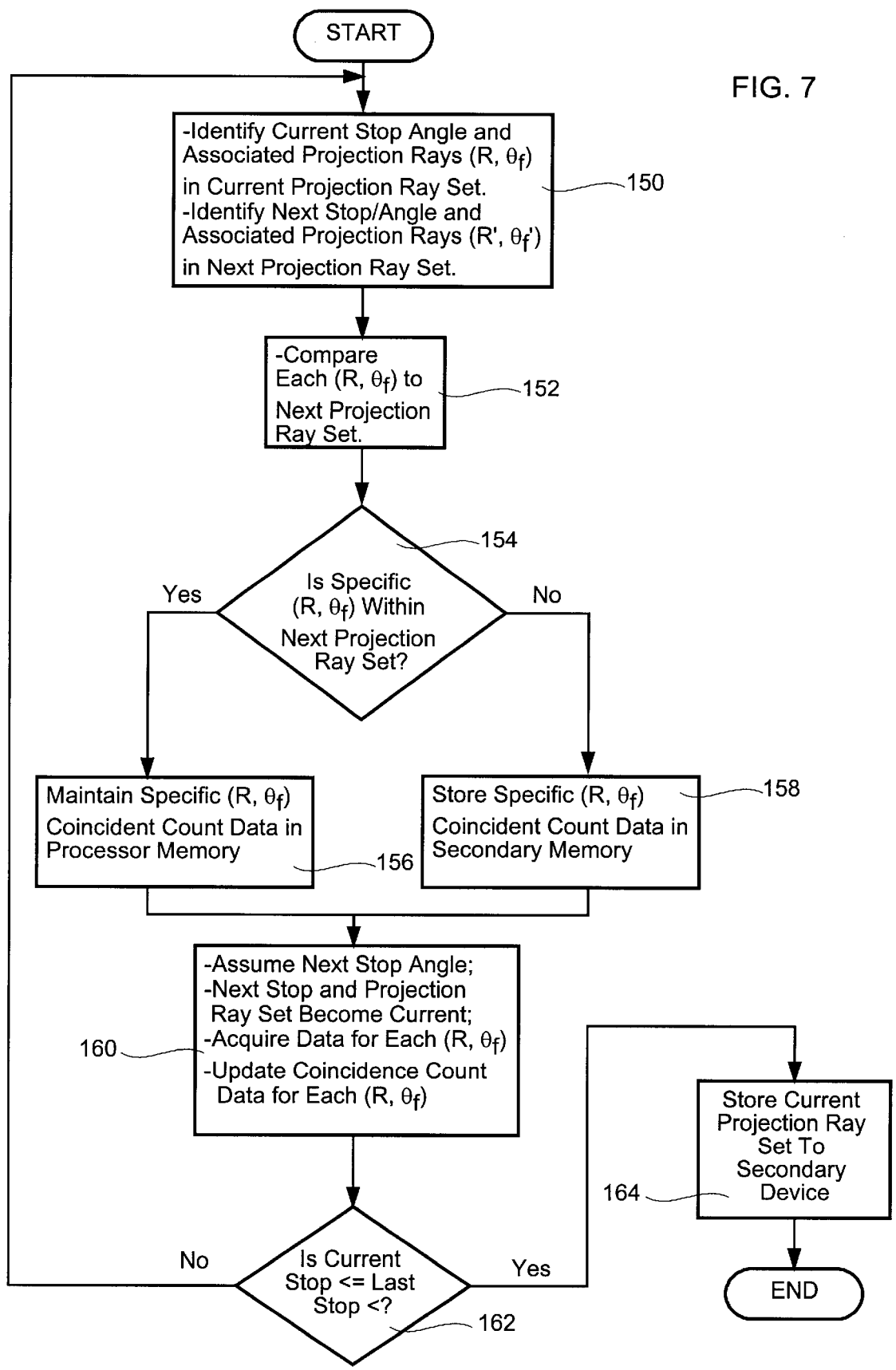
FIG. 7 is a flow chart illustrating a preferred embodiment of the inventive method.

The primary purpose of sorter 34 is to efficiently store coincidence data packets thereby reducing required processor memory while maintaining data integrity. The set of all projection rays which have identical flight path angles θf and pass through the camera FOV is a "profile view". A distance R between a particular projection ray and a center 114 of the FOV locates that projection ray within the FOV. As shown in FIG. 7, for example, a positron annihilation 116 occurs along a projection ray 118 which is located in a view at the projection ray angle θf and the distance R. Sorter 108 counts all events which occur on this projection ray (R, θf) during an acquisition period by sorting out the coincidence data packets which occur between camera locations along projection ray 118.

In the interest of simplifying this explanation, it will be assumed that, in order to collect coincidence count data for all possible projection angles [31] f about imaging area 98, cameras 12 and 14 are rotated in a clockwise direction and parked at discrete stop angles. The entire acquisition time is referred to as an acquisition session and the time required to acquire coincident count data at each stop angle is referred to as an acquisition period. Consecutive stop angles are separated by 2°. Rotation about area 98 begins at the initial position illustrated in FIG. 7 which is arbitrarily referred to as the initial or 0° angle position. Rotation ends at 178° after an essentially half gantry rotation about central point 114 and after data has been acquired from 90 different stop angles (i.e. 180°/2°=90 stop angles).

During a data acquisition, the coincidence counts (e.g. there is a separate coincidence count for each projection ray (R, θf)) are organized in memory 43 as a set of two-dimensional arrays, one for each axial image (in the z direction), and each having as one of its dimensions the projection ray angle θf and the other dimension the distance R. This θf by R map of detected events is called a histogram.

Coincidence events occur at random and sorter 108 quickly determines the projection ray angle θf and R values from the two locations in each coincidence data packet and increments the coincident count of the corresponding histogram array element. The values of θf and R may be calculated as follows:

$$\theta f = \arctan([W/DM][M-1-(x_1+x_2)]) \quad (1)$$

$$R = (W/2M)(x_1-x_2)\cos\theta f \quad (2)$$

where
M = number of separate detector locations identifiable by each detector along width W;
$x_1, x_2$ = head indexes on first and second detectors, respectively; and
D = Detector separation distance.

During data acquisition, sorter 108 maintains some coincident count data in processor memory 110 and transfers some coincident count data to secondary storage device 86. The method by which sorter 108 determines which data to maintain and which to store to device 86 is described in more detail below. After an acquisition session has been completed all coincident count data is stored on secondary device 86.

Array processor 88 reconstructs an image from the coincident count data in device 86. First, however, a number of corrections are made to the acquired data to correct for measurement errors such as those caused by attenuation of the gamma rays by the patient, detector gain nonuniformities, randoms and integrator deadtime. Each row of the corrected histogram array is filtered and the filtered data is then back projected to form an image array which is also stored in device 86. The filtering an back-projecting processes are also described in more detail below. The image array can then be accessed for viewing via work station 90.

Station 90 includes a CPU 120, a CRT display 122 and a keyboard 124. CPU 120 connects to network 100 and scans key board 124 for input information. Through keyboard 124 and associated control panel switches, an operator can control calibration of the system 82, its configuration, and the positioning of the patient table during an acquisition period.

II. BINNING METHOD

Figure 1:
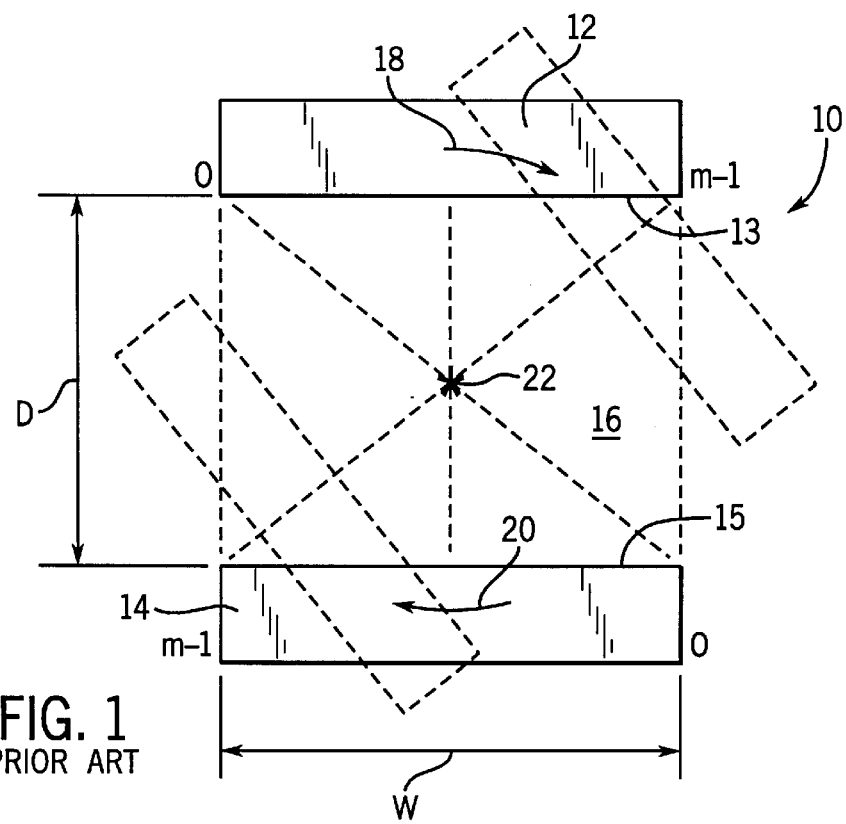
FIG. 1 is a schematic representation of a dual head PET camera configuration.
Figure 2:
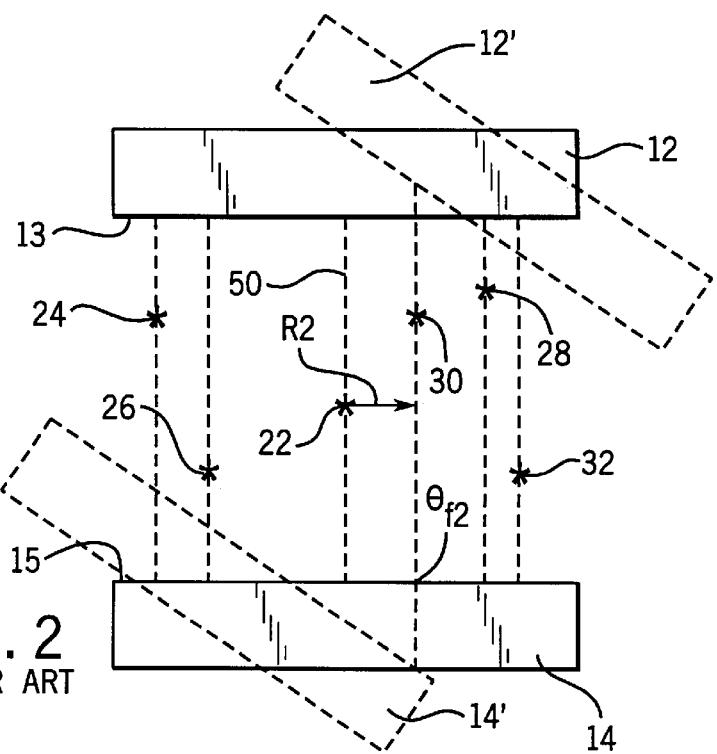
FIG. 2 is a schematic similar to FIG. 1, albeit illustrating slightly different information.
Figure 3:
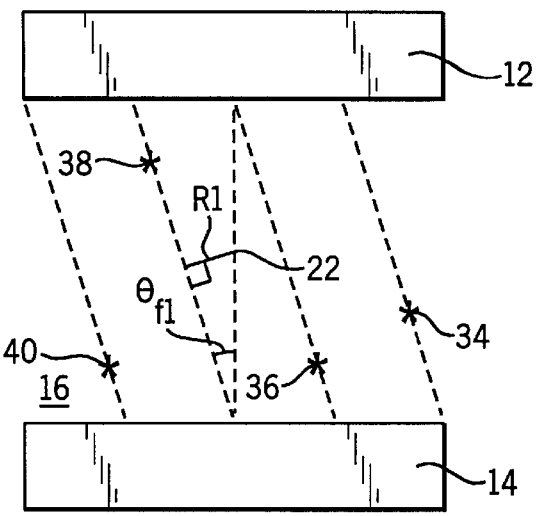
FIG. 3 is similar to FIG. 1, albeit illustrating slightly different information.
Figure 5:
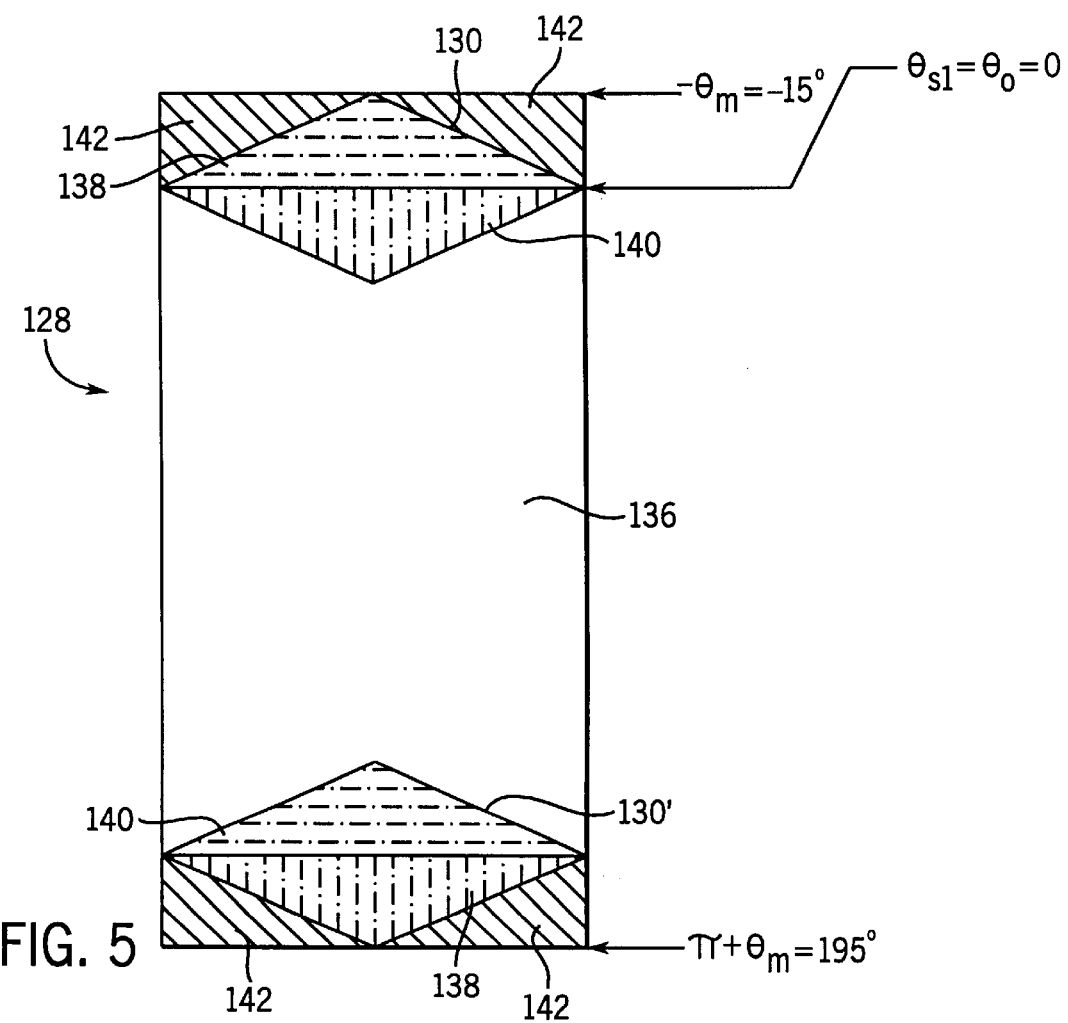
FIG. 5 is similar to FIG. 4, albeit illustrating a non-compact histogram according to the present invention.

Referring to FIG. 5, according to the present invention coincident count data is acquired in a non-compact histogram 128 over a range from −θm to π+θm. Where θm is 15°, histogram 128 ranges between −15° and 195°. To this end, at the initial position illustrated in FIG. 6 which corresponds to a first stop angle θs1, data is collected into the diamond-shaped region 130 at the top of histogram array 128. As cameras 12 and 14 are rotated to different stop angles in the clockwise direction, the data collecting "active" diamond shaped region 130 progresses down array 128 until region 130 is reached at the bottom of array 128 at the final stop angle as illustrated by diamond shaped region 130'. The resulting non-compact histogram array 128 consists of several regions which can generally be grouped into the following types:

1. Projection rays where all count data for the projection ray (R, θf) has been acquired and stored into a corresponding data element, these rays collectively referred to by numeral 136;

2. Projection rays at angles outside the range from 0 to 180° for which some but not all count data has been acquired and stored into a corresponding data element, these rays collectively referred to by numeral 138;
3. Projection rays within the range from 0 to 180° for which some but not all count data has been acquired and stored into a corresponding data element, these rays collectively referred to by numeral 140; and
4. Projection rays for which no coincident count data is collected and for which corresponding data elements contain exactly zero counts, these rays collectively referred to by the numeral 142.

Figure 4:
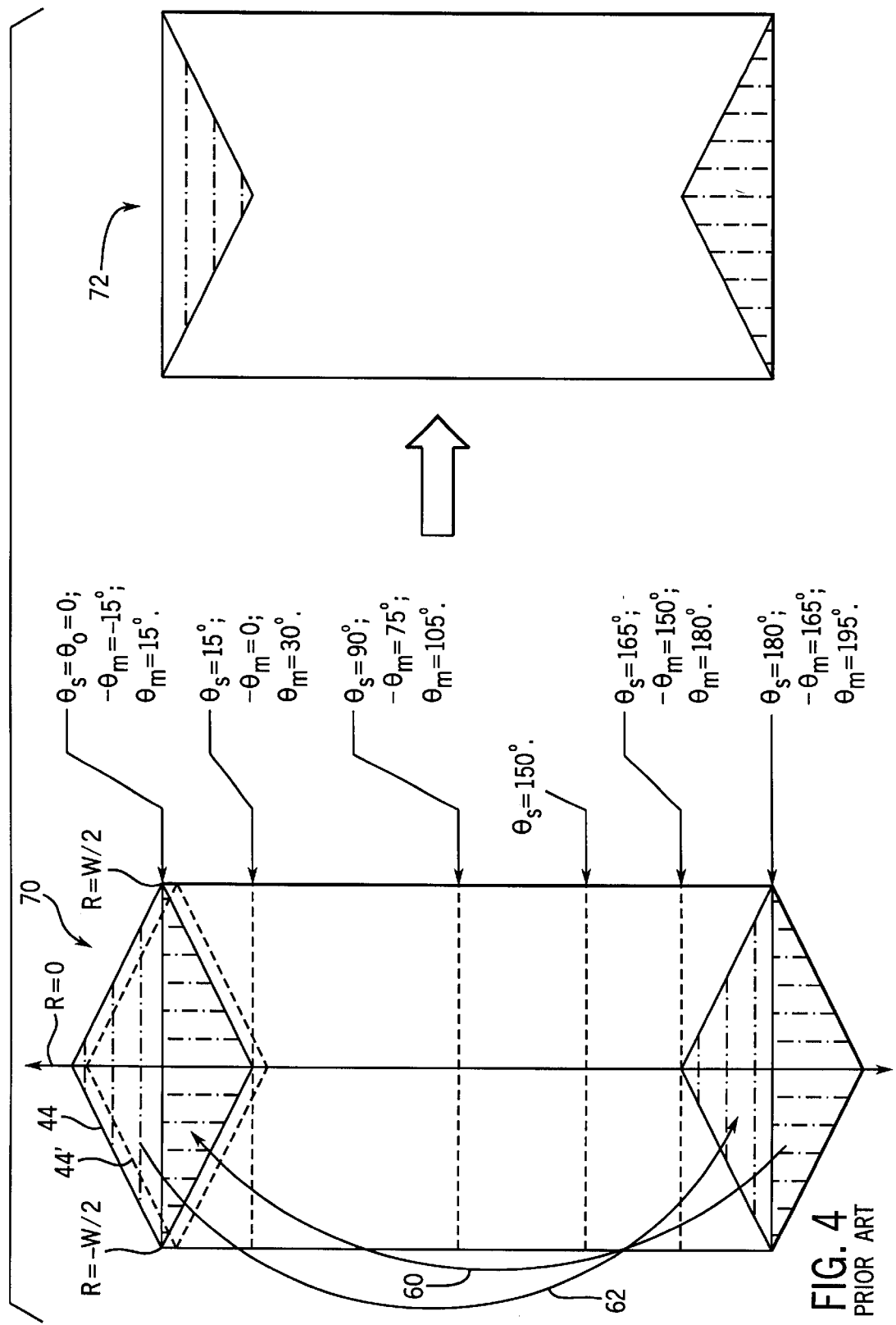
FIG. 4 is a schematic representation of a prior art histogram before and after compacting.

Referring to FIGS. 4 and 5, clearly array 128 is larger than compact array 70. Array 130 is larger than array 70 by a factor of 1+(2θm/π). In the present case where θm is 15°, array 130 is 1.1667 times as large as array 70. However, according to the present invention, as data acquisition at each stop angle is completed, several rows of array 130 are moved from processor memory 110 to secondary storage device 86.

Specifically, according to the present invention, after data is acquired at a specific stop angle which corresponds to a set of projection rays, sorter 108 determines, for each projection ray (R, θf) in the set, if data will be acquired during data acquisition at the next stop angle. If data for a specific projection ray (R, θf) will be acquired during data acquisition at the next stop angle, sorter 108 maintains the projection ray coincident count data in memory 110. However, if data for a specific projection ray (R, θf) will not be acquired during data acquisition at the next stop angle, sorter 108 stores the projection ray coincident count data in for the specific projection ray in storage device 86 and purges the projection ray coincident count data in for the specific projection ray from memory 110. The inventive process is illustrated in FIG. 7.

Referring to FIG. 7, initially it is assumed that data acquisition has already occurred at at least a current stop angle θs. Starting at process block 150 sorter 108 identifies the current stop angle θs which is the stop angle θs at which the cameras are currently parked. In addition, at block 150, sorter 108 identifies projection rays (R, θf corresponding to the current stop angle and at which data has been acquired during the most recent acquisition period. Moreover, at block 150 sorter 108 identifies the next stop angle which is the stop angle at which the cameras will be parked during the next data acquisition period and also identifies projection rays (R', θf) corresponding to the next stop angle and at which data will be acquired during the next acquisition period.

At process block 152 sorter 108 compares each projection ray (R, θf) which is associated with the current stop angle to the projection rays (R', θf) in the next projection ray set to determine if each projection ray (R, θf) is in the next projection ray set. At decision block 154, if a specific ray (R, θf) is in the next projection ray set meaning that data will be acquired during the next acquisition period which corresponds to the specific ray (R, θf), sorter control passes to process block 156. If a specific ray (R, θf) is not in the next projection ray set meaning that data will not be acquired during the next acquisition period which corresponds to the specific ray (R, θf), sorter control passes to process block 158.

At block 156 sorter 108 maintains specific ray (R, θf) coincident count data in processor memory 110. At block 158 sorter 108 stores specific ray (R, θf) coincident count data in secondary storage device 86 and purges the specific ray (R, θf) coincident count data from memory 110 thereby freeing memory 110 for other purposes. After each of blocks 156 and 158 control passes to block 160.

At block 160 cameras 12 and 14 are rotated to the next stop angle and sorter 108 resets the current stop angle and associated projection array set to equal the next stop angle and associated projection ray set. In addition, at block 160 cameras 12 and 14 cooperate with ALC circuitry 106 to acquire data for each projection ray (R, θf) in the new current projection ray set. Sorter 108 uses the new data to update the coincident counts associated with each ray (R, θf).

At decision block 162 sorter 108 determines if the current stop angle is the last stop angle. In the present case, the last stop angle is 178°. If the current stop angle is not the last stop angle control passes back up to process block 150 and the process begins again. If the current stop angle is the last stop angle so that all data required to generate an image has been acquired, control passes to block 164. At block 164 the current projection ray set is stored to secondary storage device 86.

Referring again to FIG. 5, at the initial stop angle θs1 memory 110 must only provide sufficient storage space to accommodate counters for all possible projection rays within the range between −θm and θm. In the present case that means that storage space for rays throughout only a 30 degree range is required. Similarly, as cameras 12 and 14 are rotated to different stop angles to acquire data, the total range of data which must be supported always remains 30°. For example, when the stop angle is changed from the first angle (i.e. 0°) to the second angle by 2° of rotation, range −θm through θm changes to −13 to 17° and projection rays corresponding to the first 2° (i.e. between −15 and −13°) are stored to secondary device 86.

Clearly, using the inventive method processor memory 110 is substantially reduced. Generally, using the present invention memory 110 size will be reduced by a factor of 180/2θm. Thus, in the present case where m is 15°, memory 110 is reduced by a factor of 6.

III. IMAGE CONSTRUCTION

After an entire acquisition period when all imaging data has been collected and is stored on secondary device 86, one of two general procedures may be performed which are consistent with the present invention. First, it would be possible to transform the acquired data array 128 into a compact array over the range from 0 to 180° as described above with respect to the prior art. Methods to achieve such a transformation are known in the art and therefore will not be explained again here in detail.

Second, a suitably configured filtered back projection process can backproject each profile view to construct an image, the back projection process accomplishing the addition of projection rays which are outside the 180 degree histogram to associated rays within the histogram. This back projection process has the same effect on a reconstructed image as combining the non-compact histogram data into a compact form prior to image reconstruction. This is because filtered back projection is a linear operation, so the filtered back projection operation can be distributed through the projection combining step.

Mathematically, filtered back projection can be expressed as follows. A true histogram row $P_\theta(r)$ includes both the θf and θf±π rows of histogram 128, given by the expression $D\theta(r)+D\theta\pm\pi(-r)$, where the plus or minus is chosen as appropriate for the target row of the histogram. Assuming the filtering and back projection operations are denoted by the letters F and B respectively, the effect of the true histogram row on an image can be expressed by the relationship:

$$BFP_{74}(r)=BF\{D_\theta(r)+D_{74}\pm\pi(-r)\}=BFD_{74}(r)+BFD_{74}\pm\pi(-r) \quad (3)$$

Thus, by filtering and backprojecting two separate coincident counts sets which corresponds to a single projection row, the resulting data merge. Note that Equation 3 relies on good linearity of the filtered back projection operation. In this method filtering the incomplete projections generates artifacts which must cancel out exactly in the back projection process.

It should be understood that the methods and apparatuses described above are only exemplary and do not limit the scope of the invention, and that various modifications could be made by those skilled in the art that would fall under the scope of the invention. For example, while the invention is described as one wherein, when data will not be acquired for a projection ray during a next consecutive acquisition period at a next stop angle, the coincident count data for the projection ray is stored in secondary storage and purged from memory 110, the invention also contemplates another method wherein, only if no more data will be collected for a projection ray during the remainder of an acquisition session, will the sorter store the projection ray data in the secondary device. Thus, referring again to FIG. 5, data corresponding to the range between −15 and 15° would remain in memory 110 until the end of the acquisition session. During the last 30° of data acquisition the data corresponding to the first 30° would be supplemented. While this solution may not be as advantageous as the preferred solution it does still reduce memory size. For example, in the present example, memory 110 would only have to support 60° of data instead of the entire 180° as in the prior compact histogram example.

To apprise the public of the scope of this invention, we make the following claims:

What is claimed is:

1. A method to be used with an imaging system, the system including two opposed cameras mounted for rotation among a plurality of acquisition angles about an imaging axis for acquiring imaging data throughout an arc about the axis, the cameras collecting data corresponding to an acquisition angle range including a plurality of flight path angles at each acquisition angle, the system also including a processor having a processor memory and a secondary memory, the method for reducing the amount of processor memory required to acquire imaging data, the method comprising the steps of:

(a) after gathering imaging information at an acquisition angle, for each flight path angle within the acquisition angle range, determining if additional data will be collected during acquisition at the next consecutive Q acquisition angles;

(b) where imaging data for a flight path angle will be collected during data acquisition at least one of the next Q acquisition angles, maintaining imaging data for the flight path angle in the processor memory; and (c) where imaging data for a flight path angle will not be collected during data acquisition at least one of the next Q acquisition angles, storing the imaging data in the processor memory for the flight path angle in the secondary memory.

2. The method of claim 1 wherein each of the cameras includes a flat impact surface and the impact surfaces are parallel and the method further includes the steps of, prior to determining, identifying the next consecutive acquisition angle range.

3. The method of claim 2 wherein, during acquisition the cameras are parked at specific stop angles θs and the step of identifying includes determining the acquisition angle range as a function of the stop angle.

4. The method of claim 1 wherein Q is equal to the number of remaining stop angles θs at which imaging data is to be gathered.

5. The method of claim 1 wherein Q is 1.

6. The method of claim 2 wherein each impact surface is characterized by a width W which extends between first and second opposite surface edges, the cameras mounted such that the first edges and second edges of each camera oppose each other, respectively, the cameras mounted for 180° of rotation about the imaging axis, when the cameras are in an initial position an initial system axis passes through the imaging axis and is perpendicular to each of the impact surfaces bisecting each impact surface and forming an initial system angle, an acquisition angle defined by the initial angle plus some offset angle, an extreme negative flight path angle defined by the angle formed by the acquisition angle and a plane which extends between the first edge of the first camera impact surface and the second edge of the second camera impact surface and an extreme positive flight path angle defined by the angle formed by the acquisition angle and a plane which extends between the second edge of the first camera impact surface and the first edge of the second camera impact surface, the acquisition angle range being among the angles between the extreme maximum and minimum flight path angles.

7. The method of claim 6 wherein the acquisition angle range is defined by the extreme maximum and minimum flight path angles.

8. The method of claim 1 also for, after the imaging data has been stored in the secondary memory, constructing an image using the stored imaging data, the method further including the steps of, filtering the imaging data and backprojecting the data to construct the image.

9. The method of claim 1 wherein the imaging system is a PET system.

10. An apparatus for use with an imaging system including two opposed cameras mounted for rotation among a plurality of acquisition angles about an imaging axis for acquiring imaging data throughout an arc about the axis, the cameras collecting data corresponding to an acquisition angle range including a plurality of flight path angles at each acquisition angle, the system also including a processor having a processor memory and a secondary memory, the apparatus for reducing the amount of processor memory required to acquire imaging data, the apparatus comprising:

a programmed data processor for:

(a) after gathering imaging information at an acquisition angle, for each flight path angle within the acquisition angle range, determining if additional data will be collected during acquisition at the next consecutive Q acquisition angles;

(b) where imaging data for a flight path angle will be collected during data acquisition at least one of the next Q acquisition angles, maintaining imaging data for the flight path angle in the processor memory; and (c) where imaging data for a flight path angle will not be collected during data acquisition at least one of the next Q acquisition angles, storing the imaging data in the processor memory for the flight path angle in the secondary memory.

11. The apparatus of claim 10 wherein each of the cameras includes a flat impact surface and the impact surfaces are parallel and the processor further performs the steps of, prior to determining, identifying the next consecutive acquisition angle range.

12. The apparatus of claim 11 wherein, during acquisition the cameras are parked at specific stop angles and wherein the processor identifies by determining the acquisition angle range as a function of the stop angle.

13. The apparatus pf claim 10 wherein Q is equal to the number of remaining stop angles at which imaging data is to be gathered.

14. The apparatus of claim 10 wherein Q is 1.

15. The apparatus of claim 11 wherein each impact surface is characterized by a width which extend between first and second opposite surface edges, the cameras mounted such that the first edges and second edges of each camera oppose each other, respectively, the cameras mounted for 180° of rotation about the imaging axis, when the cameras are in an initial position an initial system axis passes through the imaging axis and is perpendicular to each of the impact surfaces bisecting each impact surface and forming an initial system angle, an acquisition angle defined by the initial angle plus some offset angle, an extreme negative flight path angle defined by the angle formed by the acquisition angle and a plane which extends between the first edge of the first camera impact surface and the second edge of the second camera impact surface and an extreme positive flight path angle defined by the angle formed by the acquisition angle and a plane which extends between the second edge of the first camera impact surface and the first edge of the second camera impact surface, the acquisition angle range being among the angles between the extreme maximum and minimum flight path angles.

16. The apparatus of claim 15 wherein the acquisition angle range is defined by the extreme maximum and minimum flight path angles.

17. The apparatus of claim 10 wherein the imaging system is a PET system.

* * * * *